(12) United States Patent
Carlson et al.

(10) Patent No.: US 7,131,234 B2
(45) Date of Patent: Nov. 7, 2006

(54) COMBINATION END SEAL AND RESTRAINT

(75) Inventors: William C. Carlson, Olympia, WA (US); Jeffrey E. Hartle, Tacoma, WA (US); Michael K. McKinnis, Chehalis, WA (US); Curtis A. Bryan, Olympia, WA (US); Patrick Gaillard, Bayville, NY (US); Edwin Hirahara, Federal Way, WA (US); Paul G. Gaddis, Seattle, WA (US); Katherine M. Salatas, Tacoma, WA (US)

(73) Assignee: Weyerhaeuser Co., Federal Way, WA (US)

( * ) Notice: Subject to any disclaimer, the term of this patent is extended or adjusted under 35 U.S.C. 154(b) by 239 days.

(21) Appl. No.: 10/982,952

(22) Filed: Nov. 4, 2004

(65) Prior Publication Data

US 2005/0114919 A1 May 26, 2005

Related U.S. Application Data

(60) Provisional application No. 60/525,432, filed on Nov. 25, 2003.

(51) Int. Cl.
*A01C 21/00* (2006.01)
*A01C 1/06* (2006.01)
(52) U.S. Cl. ..................... 47/57.6; 47/DIG. 9
(58) Field of Classification Search ............ 47/57.6, 47/DIG. 9
See application file for complete search history.

(56) References Cited

U.S. PATENT DOCUMENTS

| 2,309,702 A | 2/1943 | Kirschenbaum |
| 2,502,809 A | 4/1950 | Vogelsang |
| 2,809,772 A | 10/1957 | Weisz |
| 3,034,905 A | 5/1962 | Weintraub et al. |
| 3,098,320 A | 7/1963 | Estkowski |
| 3,545,129 A | 12/1970 | Schreiber et al. |
| 3,688,437 A | 9/1972 | Hamrin |
| 3,690,034 A | 9/1972 | Knapp |
| 3,734,987 A | 5/1973 | Hamrin |
| 3,850,753 A | 11/1974 | Chibata et al. |
| 4,147,930 A | 4/1979 | Browne et al. |
| 4,166,006 A | 8/1979 | Hertl et al. |
| 4,252,827 A | 2/1981 | Yokoyama et al. |
| 4,465,017 A | 8/1984 | Simmons |
| 4,562,663 A | 1/1986 | Redenbaugh |
| 4,583,320 A | 4/1986 | Redenbaugh |
| 4,615,141 A | 10/1986 | Janick et al. |
| 4,628,633 A | 12/1986 | Nilsson |

(Continued)

FOREIGN PATENT DOCUMENTS

CA 1241552 9/1988

(Continued)

OTHER PUBLICATIONS

Adlercreutz, P., and B. Mattiasson, "Oxygen Supply to Immobilized Cells: 1. Oxygen Production by Immobilized *Chlorella pyrenoidosa*," *Enzyme Microbial Technol.* 4:332-336, 1982.

(Continued)

*Primary Examiner*—Kent Bell
(74) *Attorney, Agent, or Firm*—Christensen O'Connor Johnson Kindness (57) ABSTRACT

A combination end seal and cotyledon restraint (20) for an artificial seed (22) is provided. The combination end seal and cotyledon restraint includes a cap portion (30) sized to substantially seal one end of an artificial seed and a cotyledon restraint (32) unitarily formed with the cap portion.

26 Claims, 7 Drawing Sheets

U.S. PATENT DOCUMENTS

| | | | |
|---|---|---|---|
| 4,665,648 | A | 5/1987 | Branco et al. |
| 4,715,143 | A | 12/1987 | Redenbaugh et al. |
| 4,769,945 | A | 9/1988 | Motoyama et al. |
| 4,777,762 | A | 10/1988 | Redenbaugh et al. |
| 4,777,907 | A | 10/1988 | Sänger |
| 4,779,376 | A | 10/1988 | Redenbaugh |
| 4,780,987 | A | 11/1988 | Nelson et al. |
| 4,802,305 | A | 2/1989 | Kojimoto et al. |
| 4,802,905 | A | 2/1989 | Spector |
| 4,806,357 | A | 2/1989 | Garrett et al. |
| 4,808,430 | A | 2/1989 | Kouno |
| 4,866,096 | A | 9/1989 | Schweighardt |
| 4,879,839 | A | 11/1989 | Gago et al. |
| 5,010,685 | A | 4/1991 | Sakamoto et al. |
| 5,044,116 | A | 9/1991 | Gago et al. |
| 5,181,259 | A | 1/1993 | Rorvig |
| 5,183,757 | A | 2/1993 | Roberts |
| 5,236,469 | A | 8/1993 | Carlson et al. |
| 5,250,082 | A | 10/1993 | Teng et al. |
| 5,258,132 | A | 11/1993 | Kamel et al. |
| 5,284,765 | A | 2/1994 | Bryan et al. |
| 5,427,593 | A | 6/1995 | Carlson et al. |
| 5,451,241 | A | 9/1995 | Carlson et al. |
| 5,464,769 | A | 11/1995 | Attree et al. |
| 5,529,597 | A | 6/1996 | Iijima |
| 5,564,224 | A | 10/1996 | Carlson et al. |
| 5,565,355 | A | 10/1996 | Smith |
| 5,666,762 | A | 9/1997 | Carlson et al. |
| 5,680,320 | A | 10/1997 | Helmer et al. |
| 5,687,504 | A | 11/1997 | Carlson et al. |
| 5,701,699 | A | 12/1997 | Carlson et al. |
| 5,732,505 | A | 3/1998 | Carlson et al. |
| 5,771,632 | A | 6/1998 | Liu et al. |
| 5,784,162 | A | 7/1998 | Carib et al. |
| 5,799,439 | A | 9/1998 | MacGregor |
| 5,821,126 | A | 10/1998 | Durzan et al. |
| 5,842,150 | A | 11/1998 | Renberg et al. |
| 5,877,850 | A | 3/1999 | Ogata |
| 5,930,803 | A | 7/1999 | Becker et al. |
| 5,960,435 | A | 9/1999 | Rathmann et al. |
| 6,021,220 | A | 2/2000 | Anderholm |
| 6,092,059 | A | 7/2000 | Straforini et al. |
| 6,119,395 | A | 9/2000 | Hartle et al. |
| 6,145,247 | A | 11/2000 | McKinnis |
| 6,470,623 | B1 | 10/2002 | Hirahara |
| 6,567,538 | B1 | 5/2003 | Pelletier |
| 6,582,159 | B1 | 6/2003 | McKinnis |
| 2002/0192686 | A1 | 12/2002 | Adorjan et al. |
| 2003/0055615 | A1 | 3/2003 | Zhang et al. |
| 2003/0101643 | A1 | 6/2003 | Hartle et al. |

FOREIGN PATENT DOCUMENTS

| | | |
|---|---|---|
| CA | 1250296 | 2/1989 |
| EP | 0 107 141 A1 | 5/1984 |
| EP | 0 300 730 A1 | 1/1989 |
| EP | 0 380 692 A1 | 8/1990 |
| EP | 0776601 A1 | 6/1997 |
| FR | 2 680 951 A1 | 3/1993 |
| JP | 61040708 | 2/1986 |
| JP | 62275604 | 11/1987 |
| JP | 63133904 | 6/1988 |
| JP | 63152905 | 6/1988 |
| JP | 2-46240 | 2/1990 |
| JP | 407179683 A | 7/1995 |
| WO | WO 91/00781 A1 | 1/1991 |
| WO | WO 91/01803 | 2/1991 |
| WO | WO 92/07457 A1 | 5/1992 |
| WO | WO 95/05064 | 2/1995 |
| WO | WO 98/33375 | 8/1998 |
| WO | WO 99/26470 | 6/1999 |

OTHER PUBLICATIONS

Adlercreutz, P., and B. Mattiasson, "Oxygen Supply to Immobilized Cells: 3. Oxygen Supply by Hemoglobin or Emulsions of Perfluorochemicals," *Eur. J. Appl. Microbiol. & Biotechnol.* 16:165-170, 1982.

Bapat, V.A., "Studies on Synthetic Seeds of Sandalwood (*Santalum album* L.) and Mulberry (*Morus indica* L.)," in K. Redenbaugh (ed.), Synseeds: *Applications of Synthetic Seeds to Crop Improvement*, CRC Press, Inc., Boca Raton, Fla., 1993, pp. 381-407.

Bapat, V.A., and P.S. Rao, "In Vivo Growth of Encapsulated Axillary Buds of Mulberry (*Morus indica* L.)," *Plant Cell, Tissue and Organ Culture* 20:69-70, 1990.

Bapat, V.A., and P.S. Rao, "Sandalwood Plantlets from 'Synthetic Seeds,'" *Plant Cell Reports* 7:434-436, 1988.

Buchenauer, H., "Mode of Action and Selectivity of Fungicides Which Interfere with Ergosterol Biosynthesis," *Proceedings of the 1977 British Crop Protection Conference—Pests and Diseases*, Brighton, U.K., 1977, pp. 699-711.

Chandler, D., et al., "Effects of Emulsified Perfluorochemicals on Growth and Ultrastructure of Microbial Cells in Culture," *Biotechnol. Letters* 9(3):195-200, 1987.

Cheng, Z., P.P. Ling, "Machine Vision Techniques for Somatic Coffee Embryo Morphological Feature Extraction," *American Society of Agricultural Engineers* 37(5):1663-1669, 1994.

Chi, C.-M., et al., "An Advanced Image Analysis System for Evaluation of Somatic Embryo Development," *Biotechnology and Bioengineering* 50:65-72, Apr. 996.

Clark, Jr., L.C., et al., "Emulsions of Perfluoronated Solvents for Intravascular Gas Transport," *Fed. Proceed.* 34(6):1468-1477, 1975.

Clark, Jr., L.C., et al., "The Physiology of Synthetic Blood," *J.Thorac. & Cardiovasc. Surg.* 60(6):757-773, 1970.

Damiano, D., and S.S. Wang, "Novel Use of Perfluorocarbon for Supplying Oxygen to Aerobic Submerged Cultures," *Biotechnol. Letters* 7(2):81-86, 1985.

Datta, S.K., and I. Potrykus, "Artificial Seeds in Barley: Encapsulation of Microspore-Derived Embryos," *Thero. Appl. Genet.* 77:820-824, 1989.

Dumet, D., et al., "Cryopreservation of Oil Palm (*Elaeis guincesis* Jacq.) Somatic Embryos Involving a Desiccation Step," *Plant Cell Reports* 12:352-355, 1993.

Dupuis, J.-M., et al., "Pharmaceutical Capsules as a Coating System for Artificial Seeds," *Bio/Technol.* 12:385-389, 1994.

Ebert, W.W., and P.F. Knowles, "Inheritance of Pericarp Types, Sterility, and Dwarfness in Several Safflower Crosses," *Crop Science* 6:579-582, 1966.

Fujii, A., et al., "Artificial Seeds for Plant Propagation," *Trends in Bio/Technol.* 5:335-339, 1987.

Fujii, J., et al., "ABA Maturation and Starch Accumulation in Alfalfa Somatic Embryos" (Abstract), *In Vitro* 25 (3, Part 2):61A, 1989.

Fujii, J., et al., "Improving Plantlet Growth and Vigor From Alfalfa Artificial Seed" (Abstract), *In Vitro* 24 (3, Part 2):70A, 1989.

Fujita, T., et al., "Fluorocarbon Emulsion as a Candidate for Artificial Blood," *Europ. Surg. Res.* 3:436-453, 1971.

Geyer, R.P., "'Bloodless' Rats Through the Use of Artificial Blood Substitutes," *Fed. Proceed* 34(6):1499-1505, 1975.

Gray, D.J., and A. Purohit, "Somatic Embryogenesis and Development of Synthetic Seed Technology," *Crit. Rev. Plant Sci.* 10(1):33-61, 1991.

Grob, J.A., et al., "Dimensional Model of Zygotic Douglas-Fir Embryo Development," *International Journal of Plant Sciences* 160(4):653-662, 1999.

Gupta, P.K., and D.J. Durzan, "Biotechnology of Somatic Polyembryogenesis and Plantlet Regeneration in Loblolly Pine," *Bio/Technol.* 5:147-151, 1987.

Ibarbia, E.A., "Synthetic Seed: Is It the Future," *Western Grower and Shipper* 59:12, 1988.

Janick, J., Production of Synthetic Seed via Desiccation and Encapsulation (Abstract), *In Vitro* 24 (3, Part 2):70A, 1989.

Kamada, H., et al., "New Methods for Somatic Embryo Induction and Their Use of Synthetic Production" (Abstract), *In Vitro* 24(3, Part 2):71A, 1988.

Kim YH, "ABA and Polyox-Encapsulation or High Humidity Increases Survival of Desiccated Somatic Embryos of Celery," *HortScience* 24(4):674-676, 1989.

King, A.T., et al., "Perfluorochemicals and Cell Culture," *Biotechnol.* 7:1037-1042, 1989.

Kitto, S.L., and J. Janick, "A Citrus Embryo Assay to Screen Water-Soluble Resins as Synthetic Seed Coats," *HortScience* 20(1):98-100, 1985.

Kitto, S.L., and J. Janick, "Production of Synthetic Seeds by Encapsulating Asexual Embryos of Carrot," *J. Amer. Soc. Hort. Sci.* 110(2):277-282, 1985.

Li, X.-Q., "Somatic Embryogenesis and Synthetic Seed Technology Using Carrot as a Model System," in K. Redenbaugh (ed.), *Synseeds: Applications of Synthetic Seeds to Crop Improvement*, CRC Press, Inc., Boca Raton, Fla., 1993, pp. 289-304.

Mattiasson, B., and P. Adlercreutz, "Use of Perfluorochemicals for Oxygen Supply to Immobilized Cells," *Ann. N.Y. Acad. Sci.* 413:545-547, 1984.

Paulet, F., et al., "Cryopreservation of Apices of *In Vitro* Plantlets of Sugarcane (Saccharum sp. Hybrids) Using Encapsulation/Dehydration," *Plant Cell Reports* 12:525-529, 1993.

Redenbaugh, K., et al., "Encapsulated Plant Embryos," *Biotechnology in Agriculture*, 1988, pp. 225-248.

Redenbaugh, K., et al., "Encapsulation of Somatic Embryos for Artificial Seed Production" (Abstract), *In Vitro* 20(2):256-257, 1984.

Redenbaugh, K., et al., "Encapsulation of Somatic Embryos in Synthetic Seed Coats," *HortScience* 22(5):803-809, 1987.

Redenbaugh, K., et al., "III.3 Artificial Seeds—Encapsulated Somatic Embryos," *Biotech. in Agr. & For.* 17:395-416, 1991.

Redenbaugh, K., et al., "Scale-Up: Artificial Seeds," in Green et al. (eds.), *Plant Tissue and Cell Culture*, Alan R. Liss, Inc., New York, 1987, pp. 473-493.

Redenbaugh, K., et al., "Somatic Seeds: Encapsulation of Asexual Plant Embryos," *Bio/Technology* 4:797-801, 1986.

Riess, J.G., and M. Le Blanc, "Perfluoro Compounds as Blood Substitutes," *Angew. Chem. Int. Ed. Engl.* 17(9):621-634, 1978.

Rogers, M., "Synthetic-Seed Technology," *Newsweek*, Nov. 28, 1983.

Sanada, M., et al., "Celery and Lettuce," in M.K. Redenbaugh (ed.), *Synseeds: Applications of Synthetic Seeds to Crop Improvement*, CRC Press, Inc., Boca Raton, Fla., 1993, pp. 305-322.

Senaratna, T., "Artificial Seeds," *Biotech. Adv.* 10(3):379-392, 1992.

Sharma SK et al., "Novel Compositions of Emulsified Perfluorocarbons for Biological Applications," *Brit. J. Pharmacol.* 89:665P, 1986.

Stuart, D.A., and M.K. Redenbaugh, "Use of Somatic Embryogenesis for the Regeneration of Plants," in H.M. LeBaron et al. (eds.), *Biotechnology in Agricultural Chemistry*, American Chemical Society, Washington, D.C., 1987, pp. 87-96.

Teasdale, R.D., and P.A. Buxton, "Culture of *Pinus radiata* Embryos With Reference to Artificial Seed Production," *New Zealand J. For. Sci.* 16(3):387-391, 1986.

Tessereau, H. et al., "Cryopreservation of Somatic Embryos: A Tool for Germplasm Storage and Commercial Delivery of Selected Plants," *Ann. Bot.* 74:547-555, 1994.

Timmis, R., "Bioprocessing for Tree Production in the Forest Industry: Conifer Somatic Embryogenesis," *Biotechnology Progress* 14(1):156-166, 1998.

Weyerhaeauser, G.H., "Biotechnology in Forestry: The Promise and the Economic Reality" *Solutions! for People, Processes and Paper* 86(10):28-30, Oct. 2003.

COMBINATION END SEAL AND RESTRAINT

CROSS REFERENCE TO RELATED APPLICATION

The present application claims the benefit of U.S. Provisional Application No. 60/525,432, filed Nov. 25, 2003.

FIELD OF THE INVENTION

The present invention relates generally to artificial seeds and, more particularly, to a combination end seal and cotyledon restraint for artificial seeds.

BACKGROUND OF THE INVENTION

Asexual propagation for plants has been shown for some species to yield large numbers of genetically identical embryos, each having the capacity to develop into a normal plant. Such embryos must usually be further cultured under laboratory conditions until they reach an autotrophic "seedling" state characterized by an ability to produce its own food via photosynthesis, resist desiccation, produce roots able to penetrate soil, and fend off soil microorganisms. Some researches have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte, and a plant embryo. A manufactured seed that does not include the plant embryo is known in the art as a "seed blank." The seed blank typically is a cylindrical capsule having a closed end and an open end. Synthetic gametophyte is placed within the seed shell to substantially fill the interior of the seed shell. A longitudinally extending hard porous insert, commonly known as a cotyledon restraint, may be centrally located within the synthetic gametophyte. The cotyledon restraint includes a centrally located cavity extending partially through its length. The cavity is sized to receive a plant embryo therein.

The well-known plant embryo includes a radicle end and a cotyledon end. The plant embryo is deposited within the cavity of the cotyledon restraint, cotyledon end first. The embryo is sealed within the seed blank by at least one end seal. There is a weakened spot in the end seal to allow the radical end of the embryo to penetrate the end seal. Thus, currently available manufactured seeds include a separate cotyledon restraint and an entirely separate end seal to seal the synthetic gametophyte within the seed shell.

Although such manufactured seeds are effective, they are not without their problems. As a non-limiting example, the manufacturing process of such seeds, while not expensive, is increased in cost by the need to design and manufacture each component of the manufactured seed, as well as the cost of assembling multiple parts. Additionally, because the cotyledon restraint is a separate subcomponent of the manufactured seed, centering the opening of the cotyledon restraint relative to the sidewalls of the seed shell requires additional manipulation either during assembly or during insertion of the embryo within the cotyledon restraint. Manufacturing artificial seeds can, therefore, be time-intensive. As a result, mass production of manufactured seeds could be made more efficient by reducing the number of parts necessary to manufacture.

Thus, there exists a need for an apparatus that combines both the end seal and the cotyledon restraint into a single apparatus, thereby eliminating the need for both a cotyledon restraint and an end seal.

SUMMARY OF THE INVENTION

A combination end seal and cotyledon restraint for an artificial seed is provided. The combination end seal and cotyledon restraint includes a cap portion sized to substantially seal one end of an artificial seed and a cotyledon restraint unitarily formed with the cap portion. In certain embodiments, the cap portion includes sidewalls sized for sealing engagement with a seed coat. In certain other embodiments, the sidewalls of the cap portion are tapered.

In yet another embodiment of the present invention, the combination end seal and cotyledon restraint includes sidewalls having an angular configuration for sealing engagement with the seed coat. In still yet other embodiments of the present invention, the sidewalls of the cap portion are sized for sealing engagement with an outside perimeter of the seed coat sidewalls.

The combination end seal and cotyledon restraint formed in accordance with the various embodiments of the present invention has advantages over a non-unitary end seal and cotyledon restraint. As a non-limiting example, a manufactured seed assembled with a combination end seal and cotyledon restraint of the present invention is simpler to manufacture. Also, because the end seal and cotyledon restraint are unitary, the location of the cotyledon restraint opening within a manufactured seed can be controlled with greater certainty than those currently available.

Thus, a combination end seal and cotyledon restraint formed in accordance with various embodiments of the present invention is more reliable and is capable of mass production at a relatively low cost.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
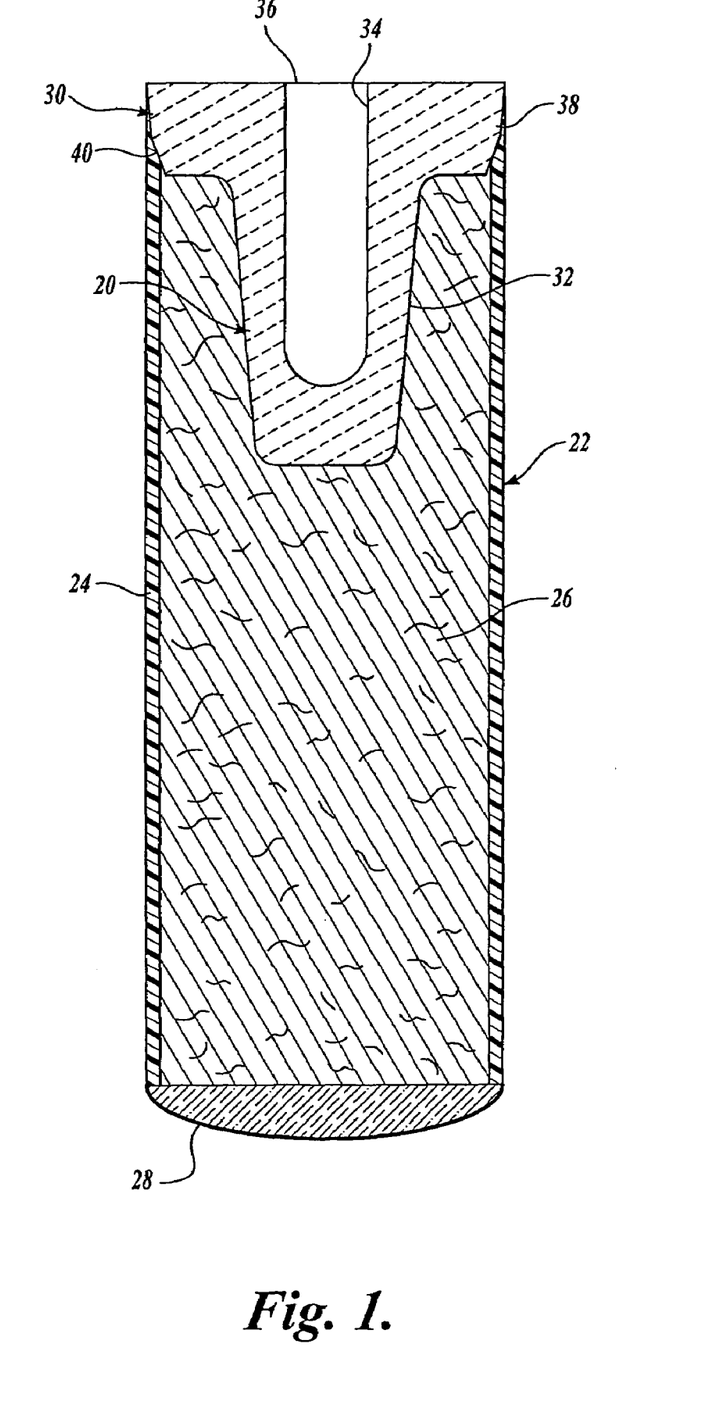
FIG. 1 is a cross-sectional side view of a manufactured seed blank having a combination end seal and cotyledon restraint formed in accordance with one embodiment of the present invention.

FIG. 1 illustrates a combination end seal and cotyledon restraint 20 (hereinafter "cylcap 20") constructed in accordance with one embodiment of the present invention. Such a cylcap 20 is suitably used for a seed blank 22, such as one as disclosed in U.S. Pat. No. 5,701,699, issued to Carlson et al., the disclosure of which is hereby expressly incorporated by reference.

The seed blank 22 includes a seed shell 24, a nutritive media 26, such as a gametophyte, and a dead end seal 28. The seed shell 24 is suitably formed from a section of tubular material. In one embodiment, the seed shell 24 is a sectioned straw of fibrous material, such as paper. The sections of straw may be pre-treated in a suitable coating material, such as wax. In other embodiments, the seed shell 24 is formed from a section of biodegradable, plastic material. It should be apparent that although sectioning tubes is preferred, other embodiments, such as obtaining tubes of appropriate size for use as manufactured seeds, are also within the scope of the present invention.

The cylcap 20 is suitably manufactured from a porous material having a hardness strong enough to resist puncture or fracture by a germinating embryo, such as a ceramic material, and includes an end seal portion 30 and a cotyledon restraint portion 32. The cotyledon restraint portion 32 is suitably integrally or unitarily formed with the end seal portion 30. The cylcap 20 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo (not shown) therein.

In certain embodiments, as the cylcap 20 is suitably manufactured from a porous material, it may be desirable to coat the cylcap 20 with a barrier material to reduce the rate of water loss and restrict or reduce microbial entry. Such barriers include wax, polyurethane, glaze, nail polish, and a coating sold by Airproducts Airflex 4514.

The end seal portion 30 is suitably circular when viewed in a top planar view and includes sidewalls 38. Although circular is the preferred embodiment of the end seal portion 30, other embodiments and shapes, such as polygonal, square, triangular, oval and other shapes, are also within the scope of the present invention.

In the embodiment of FIG. 1, the sidewalls 38 are defined by the thickness of the end seal portion 30 and has a diameter substantially equal to the inside diameter of the seed shell 24. In certain embodiments, the cylcap 24 is bonded to the seed shell 24 by heat. As a non-limiting example, during manufacturing, the cylcap 20 may be heated to a pre-determined temperature, such that when the seed shell 24 and the cylcap 20 are co-joined, heat transferred between the cylcap 20 and the seed shell 24 causes either the seed shell 24, the cylcap 20, or both to melt, thereby bonding the two together. Other methods of bonding the cylcap 20 to the seed shell 24, such as a wax bond or a hot glue melt, are also within the scope of the present invention.

As may be best seen by referring to FIG. 1, the sidewalls 38 may include a tapered portion 40. The tapered portion 40, in the illustrated embodiment of FIG. 1, may be a chamfer of one end of the end seal portion 30. The tapered portion 40 assists in assembling the cylcap 20 to the seed coat 24 during manufacturing. Although a tapered portion 40 is preferred, other embodiments, such as a cylcap that does not include a tapered portion, are also within the scope of the present invention.

Figure 2:
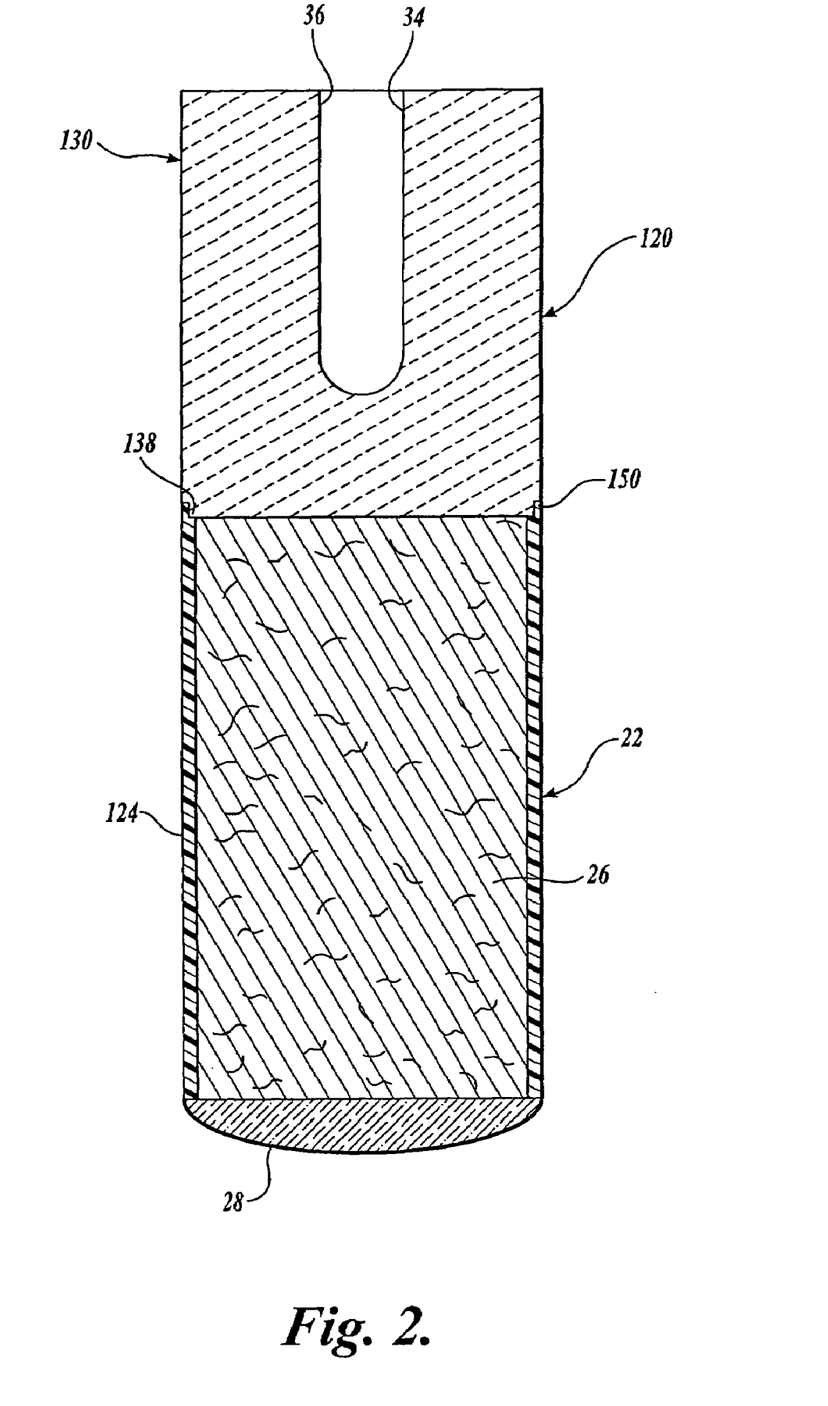
FIG. 2 is a cross-sectional side view of a manufactured seed blank having a combination end seal and cotyledon restraint formed in accordance with another embodiment of the present invention, showing sidewalls of the combination end seal and cotyledon restraint received within an outside diameter of the seed blank.

Referring now to FIG. 2, a cylcap 120 formed in accordance with another embodiment of the present invention will now be described in greater detail. The cylcap 120 of the present embodiment is identical in all aspects to the previously described embodiment, with the exception that the sidewalls 138 are an annular member formed at the bottom of the cylcap 120. It should be apparent to one of ordinary skill that terminology used throughout this detailed description such as top, bottom, side, upper, lower, etc., should be construed as descriptive, and not limiting.

In this alternate embodiment, the cotyledon restraint portion is defined by the cavity 34. The sidewalls 138 are suitably an annular, protruded area formed in the lower surface of the cylcap 120. The sidewalls extend downwardly and are configured, in one embodiment, to sealingly fit into a correspondingly shaped lip 50 formed in the upper surface of the seed shell 24. As assembled, the sidewalls 138 have a diameter that is substantially equal to the inside diameter of the seed shell 24. As a result, the sidewalls 138 of the cylcap 120 are sized and configured for sealing engagement within the outside parameter of the seed shell 224.

Although it is preferred that the sidewalls 138 are configured for sealing engagement with a correspondingly shaped lip 50 of the seed shell 224, other embodiments, such as sidewalls that sealing engage completely and/or substantially completely within the inside perimeter of the seed shell (i.e., no correspondingly shaped lip on the upper surface of the seed shell) are also within the scope of the present invention.

Figure 3:
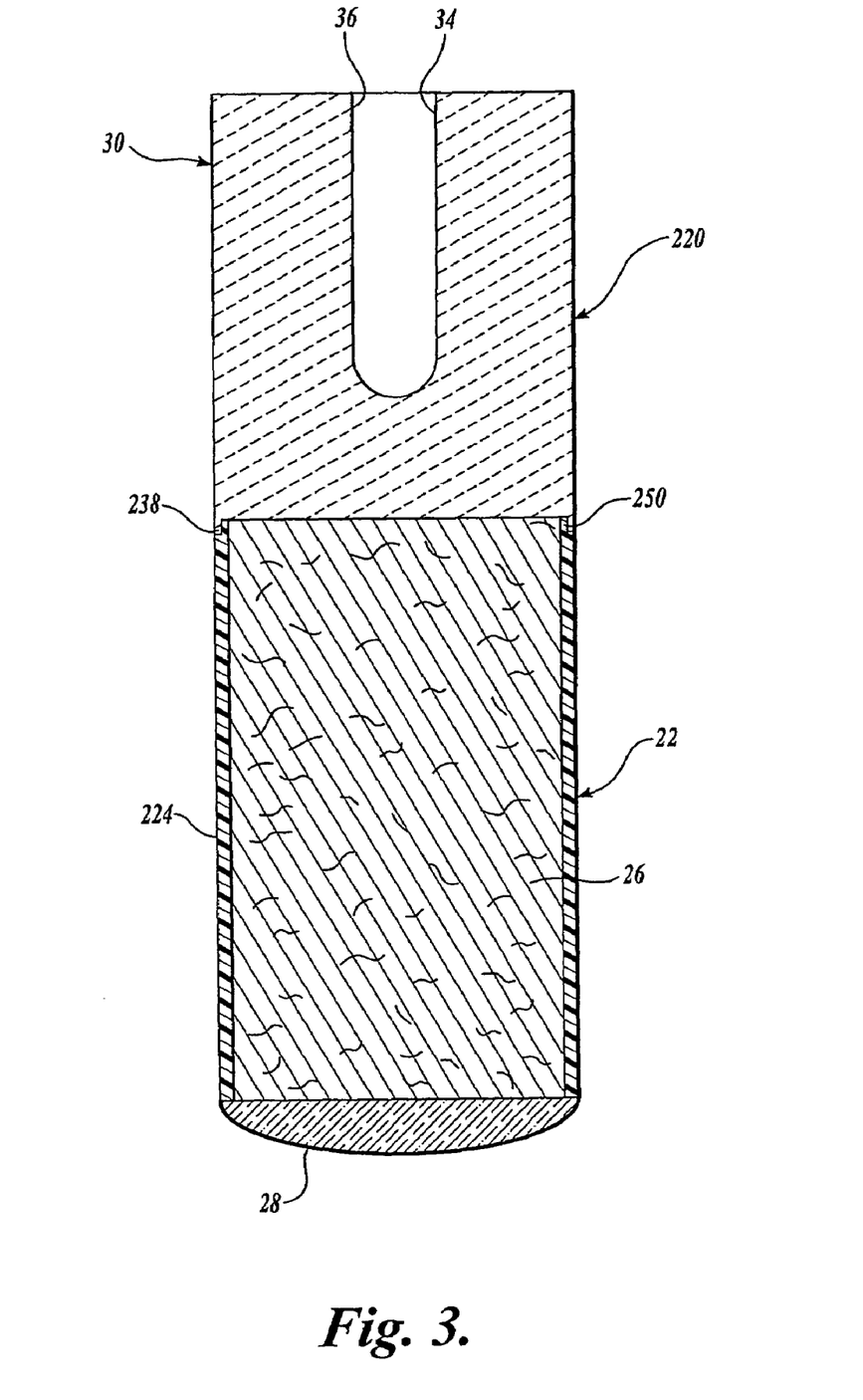
FIG. 3 is a cross-sectional side view of a manufactured seed blank having a combination end seal and cotyledon restraint formed in accordance with yet another embodiment of the present invention, showing sidewalls of the combination end seal and cotyledon restraint received around the outside diameter of the seed blank.

Referring to FIG. 3, a cylcap 220 formed in accordance with yet another embodiment to the present invention will be now be described in greater detail. The cylcap 220 of the present embodiment is identical in materials and operation as the previous cylcaps described above, with the exception that the cylcap 220 includes sidewalls 238 formed as an annular extension of the cylcap 220. Specifically, the sidewalls 238 are suitably formed as a cavity or depressed area in the lower surface of the cylcap 220.

The sidewalls 238 are suitably configured and sized to be sealingly coupled to a correspondingly shaped ridge 250 formed in the upper surface of the seed shell 224. As coupled to the seed shell 224, the sidewalls 238 have a diameter substantially equal to the outside diameter of the seed shell 224. Thus, the sidewalls 238 of the cylcap 220 are sized and configured for sealing engagement with the outside parameter of the seed shell 224.

Although it is preferred that the sidewalls 238 are configured for sealing engagement with a correspondingly shaped ridge 250, other embodiments, such as sidewalls that sealing engage completely and/or substantially completely around the outside perimeter of the seed shell (i.e., no correspondingly shaped ridge on the upper surface of the seed shell) are also within the scope of the present invention.

Figure 4:
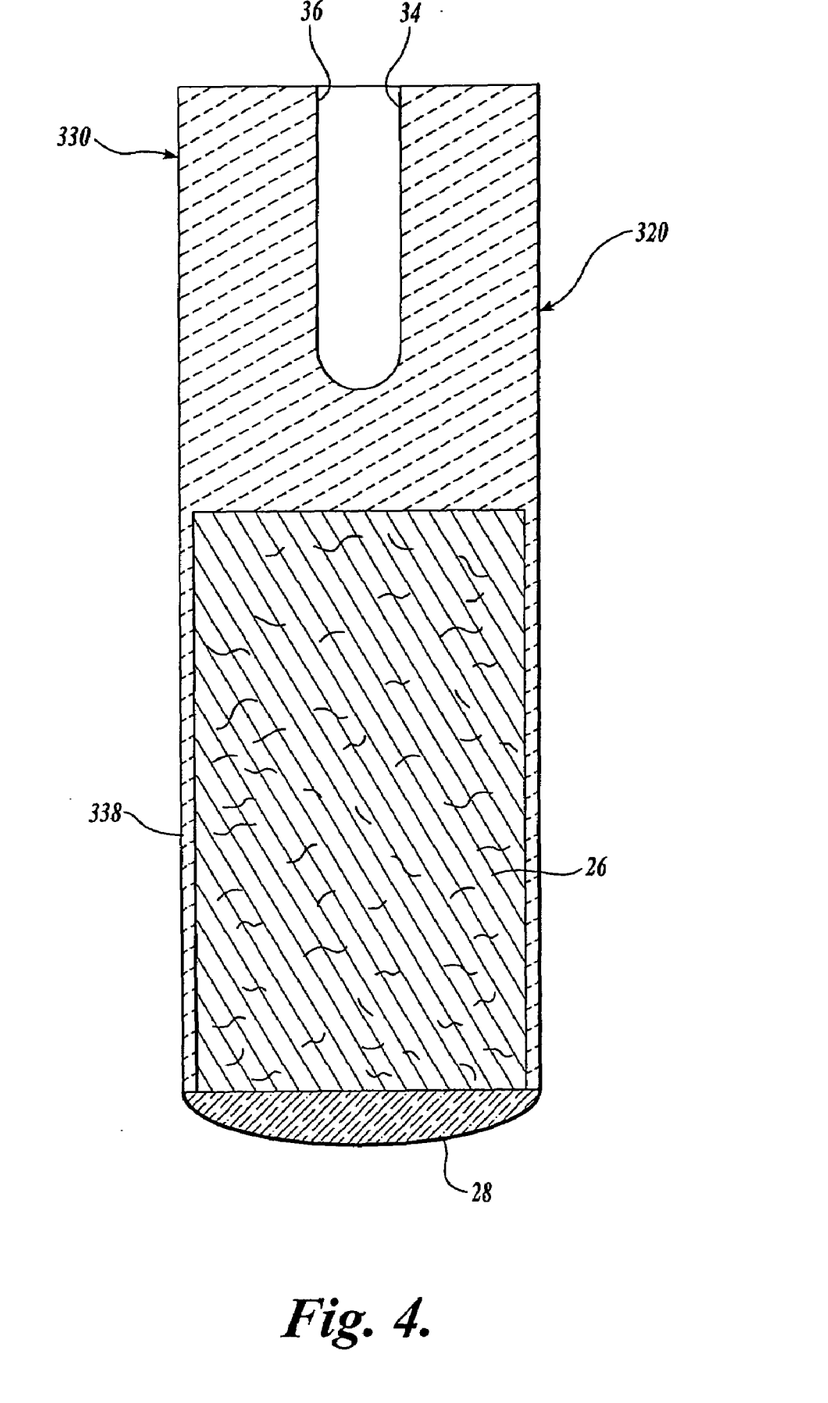
FIG. 4 is a cross-sectional side view of a manufactured seed blank having a combination end seal and cotyledon restraint formed in accordance with another embodiment of the present invention, showing sidewalls of the combination end seal and cotyledon restraint sheltering a nutritive media therein.

Referring now to FIG. 4, a cylcap 320 formed in accordance with still yet another embodiment of the present invention will now be described in greater detail. The cylcap 320 is substantially identical in materials and operation to the cylcaps previously described, with the exception that the cylcap 320 includes sidewalls 338 that reduces the need for a seed shell. Specifically, the sidewalls 338 form a housing having an interior sized to shelter nutritive media 26. In one embodiment, the cylcap 320 includes a cavity of predetermined volume extending partially through the cylcap 320. The nutritive media 26 may either be poured into the cavity defined by the sidewalls 338 or may be frozen in a shape suitable for insertion into the cavity formed by the sidewalls 338. Thus, the cylcap of the present embodiment includes sidewalls that form a housing having an interior sized and configured to shelter nutritive media 26.

As shown and described, the sidewalls 338 form a housing for nutritive media 26, thereby minimizing or eliminating the seed shell. Anywhere the sidewalls 338 are used to replace the seed shell, the exterior of the sidewalls 338 should be sealed to substantially prevent water loss and microbial entry. It should be apparent, however, that the embodiment is not intended to be so limited. As a non-limiting example, the sidewalls 338 may extend partially down the length of the nutritive media, such as one quarter, one half, three quarters, etc., of the length of the nutritive media, and couples with a correspondingly sized seed shell in a manner as set forth above. Thus, other embodiments are within the scope of the present invention.

Figure 5:
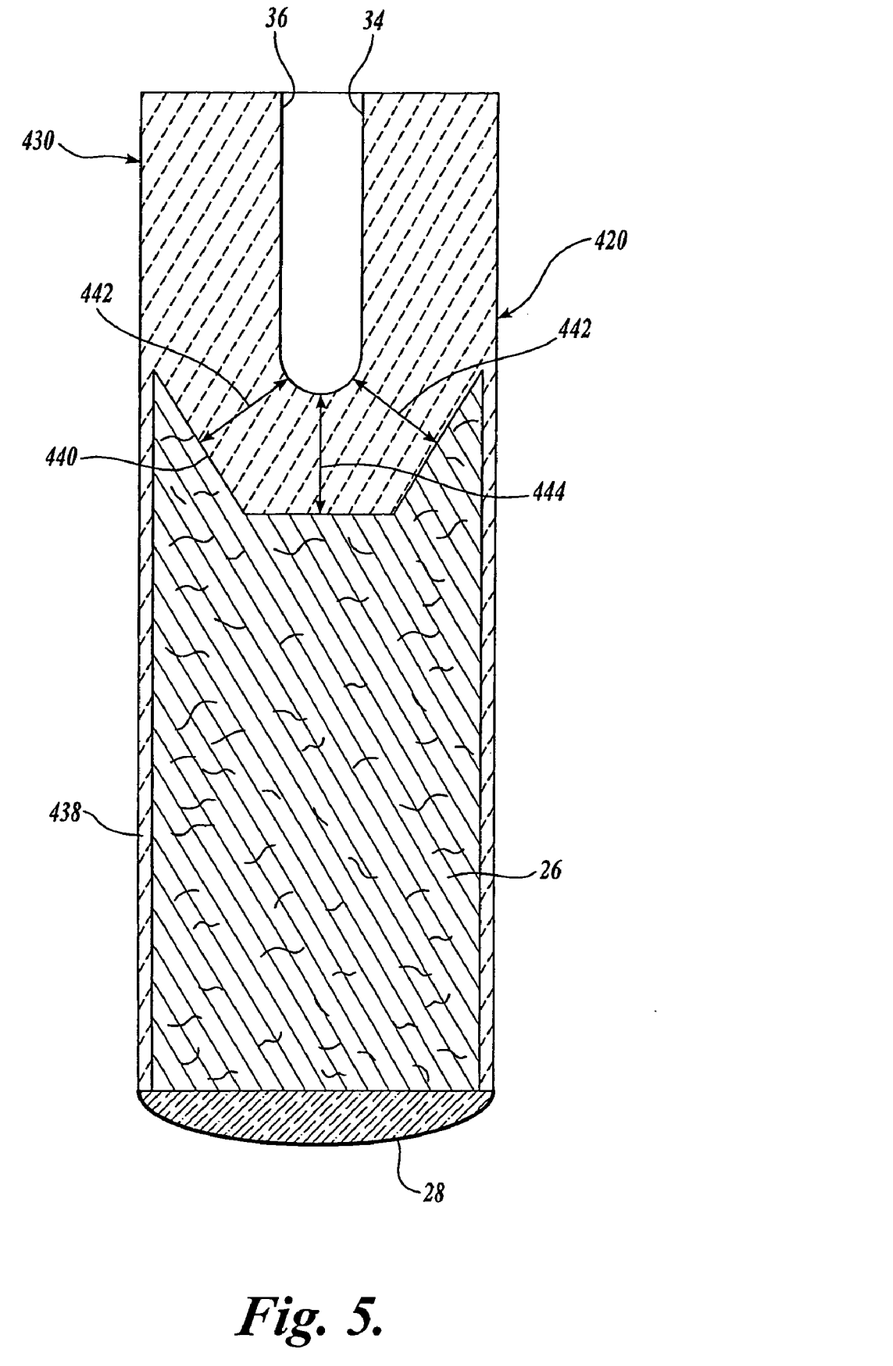
FIG. 5 is a cross-sectional side view of a manufactured seed blank having a combination end seal and cotyledon restraint formed in accordance with another embodiment of the present invention, showing the sidewalls of the combination end seal and cotyledon restraint sheltering a nutritive media therein and the interior of the combination end seal and cotyledon restraint is contoured.

Referring now to FIG. 5, a cylcap 420 formed in accordance with another embodiment to the present invention will now be described in greater detail. The cylcap 420 of FIG. 5 is identical in materials and operation to the embodiment previously described above with respect to the cylcap 320, with the exception that the interior of the cylcap 420 is contoured. Specifically, the interior includes an angled portion 440. The angled portion 440 defines a distance, indicated by the arrow 442, between the cavity 34 and the nutritive media 26 that is less than the distance, indicated by the arrow 444, without the angled portion 440. Thus, the angled portion 440 defines a shorter distance 442 for the transport of nutritive media 26 through the walls of the cylcap 420 when compared to cylcaps formed without the angled portion 440.

It should be apparent that the distance between the cavity 34 and the nutritive media 26 (indicated by the arrows 442 and 444) are illustrative only and are not intended to limit the embodiments shown and described throughout the specification. It should be apparent to one of ordinary skill that the porosity of the material used to manufacture the cylcaps shown and described throughout the present disclosure determines the acceptable distance between the cavity 34 and the nutritive media 26. As a non-limiting example, if the porosity of the cylcap is high, then the distance between the cavity 34 and the nutritive media 26 would be greater and, conversely, if the porosity is low, then the distance is smaller. Thus, such embodiments are also within the scope of the present invention.

Figure 6:
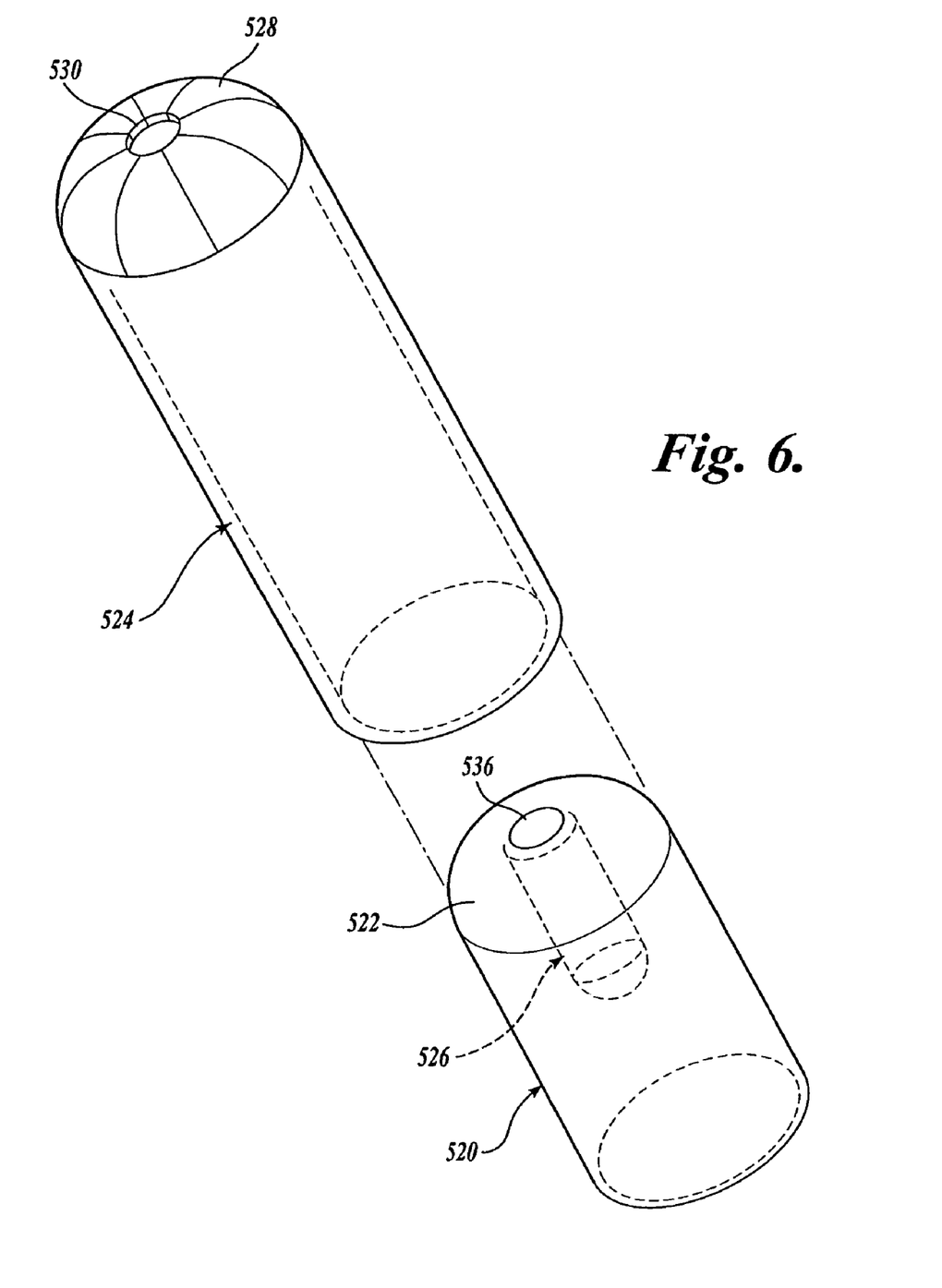
FIG. 6 is an isometric view of a manufactured seed blank having a combination end seal and cotyledon restraint formed in accordance with yet another embodiment of the present invention, showing a hollow seed shell and the combination end seal and cotyledon restraint.
Figure 7:
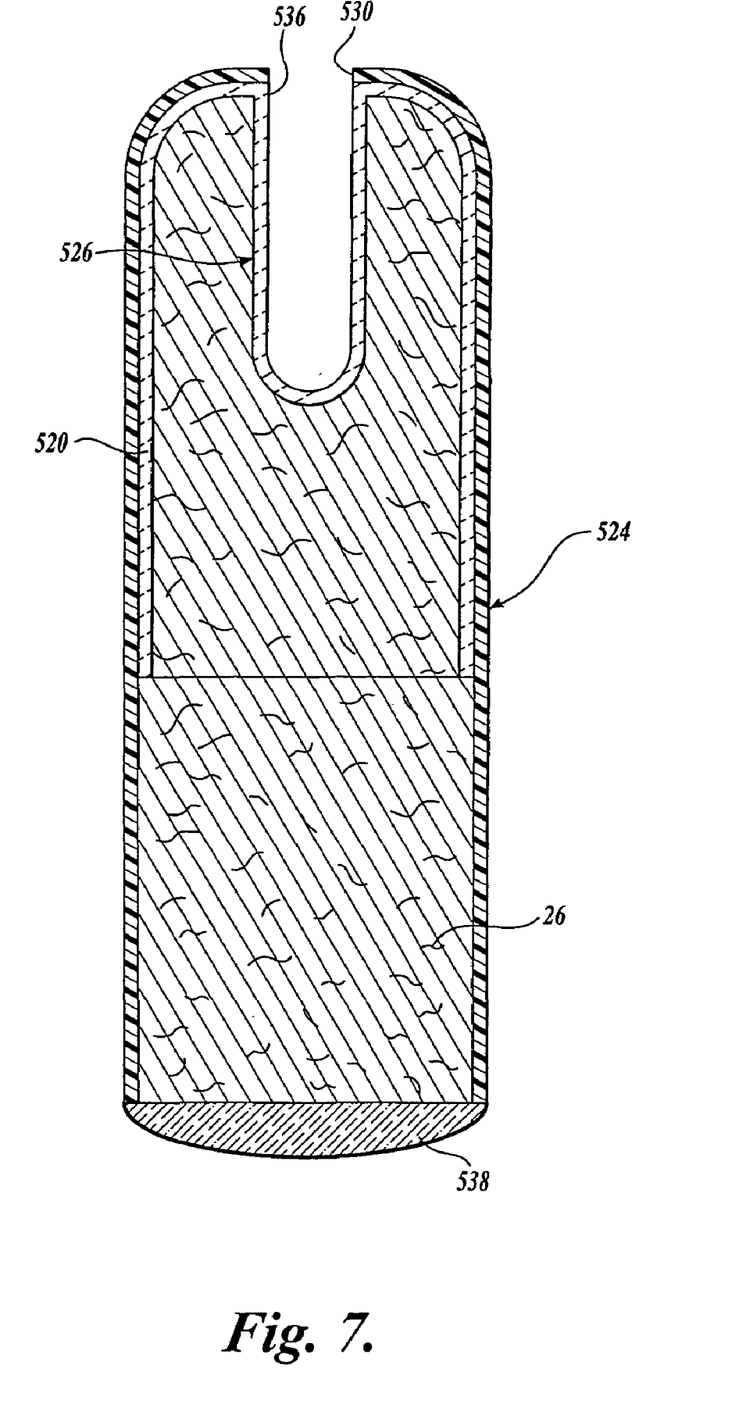
FIG. 7 is a cross-sectional side view of the manufactured seed blank of FIG. 6, showing the combination end seal and cotyledon restraint received within the seed shell and a nutritive media disposed therein.

Referring now to FIGS. 6 and 7, a cylcap 520 formed in accordance with another embodiment of the present invention will now be described in greater detail. The cylcap 520 is identical in materials and operation to the embodiments previously described above with the exception that the cylcap 520 is sized to be slidably received within a correspondingly shaped seed shell 524. The cylcap 520 is suitably formed as a bell-shaped component that is substantially hollow. The cylcap 520 includes a substantially cylindrically shaped cotyledon restraint 526 centrally located within the hollow interior of the cylcap 520, and also includes an end seal portion 522. The end seal portion 522 is suitably dome-shaped and is integrally formed with the cylcap 520. In alternate embodiments, the end seal portion 522 is a separate component that is sealingly attached to cylcap 520 in a manner well known in the art, such as by fusing and gluing.

The cotyledon restraint 526 is disposed beneath the cotyledon restraint opening 536. The cotyledon restraint 526 is integrally formed with the cylcap 520 or, in alternate embodiments, is manufactured as a separate component that is securely received within the cylcap 520.

The seed shell 524 includes a cap 528 formed at one end. The cap 528 is suitably formed by crushing or collapsing the sidewalls of one end of the seed shell 24 in any manner known in the art. The cap 528 includes an opening 530 positioned adjacent the cotyledon restraint opening 536 when the cylcap 520 is received within the seed shell 524. After the cylcap 520 is received within the seed shell 524, nutritive media 26 is suitably disposed within the seed shell 24, substantially filling the interior of both the seed shell 524 and the cylcap 520. A well known dead end seal 538 may be applied to the opened end of the seed shell 524, thereby sealing the nutritive media 26 within the seed shell 524.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A combination end seal and cotyledon restraint for an artificial seed, the combination end seal and cotyledon restraint comprising:
   (a) a cap portion sized to substantially seal one end of an artificial seed; and
   (b) a cotyledon restraint unitarily formed with the cap portion.

2. The combination end seal and cotyledon restraint of claim 1, wherein the cap portion includes sidewalls sized for sealing engagement with a seed coat.

3. The combination end seal and cotyledon restraint of claim 2, wherein the sidewalls of the cap portion are tapered.

4. The combination end seal and cotyledon restraint of claim 2, wherein the sidewalls have an annular configuration for sealing engagement with the seed coat.

5. The combination end seal and cotyledon restraint of claim 4, wherein the sidewalls of the cap portion are sized for sealing engagement with an inside perimeter of the seed coat.

6. The combination end seal and cotyledon restraint of claim 4, wherein the sidewalls of the cap portion are sized for sealing engagement an outside perimeter of the seed coat.

7. The combination end seal and cotyledon restraint of claim 1, wherein the cap portion further comprises sidewalls sized to shelter at least a portion of a nutritive media.

8. The combination end seal and cotyledon restraint of claim 7, wherein the sidewalls form a housing having an interior sized to shelter the nutritive media.

9. The combination end seal and cotyledon restraint of claim 8, wherein the interior is contoured.

10. A combination end seal and cotyledon restraint for an artificial seed, the combination end seal and cotyledon restraint comprising:
(a) an end seal portion having sidewalls; and
(b) a cotyledon restraint portion integrally formed with the end seal portion.

11. The combination end seal and cotyledon restraint of claim 10, wherein the sidewalls are contoured for sealing engagement with a seed coat.

12. The combination end seal and cotyledon restraint of claim 11, wherein the sidewalls are tapered.

13. The combination end seal and cotyledon restraint of claim 11, wherein the sidewalls are contoured to sealing engage an outside perimeter of a seed coat.

14. The combination end seal and cotyledon restraint of claim 11, wherein the sidewalls are contoured to sealing engage an inside perimeter of a seed coat.

15. The combination end seal and cotyledon restraint of claim 10, wherein the sidewalls are contoured to shelter a nutritive media.

16. The combination end seal and cotyledon restraint of claim 10, wherein the sidewalls form a housing having an interior sized and configured to shelter a nutritive media.

17. The combination end seal and cotyledon restraint of claim 10, wherein the combination end seal and cotyledon restraint is sized to be slidably received within a seed shell.

18. A combination end seal and cotyledon restraint for an artificial seed, the combination end seal and cotyledon restraint comprising:
(a) a cap portion having means for sealing; and
(b) a cotyledon restraint unitarily formed with the cap portion.

19. The combination end seal and cotyledon restraint of claim 18, wherein the means for sealing is an annular member sized and configured for sealing engagement with a seed coat.

20. The combination end seal and cotyledon restraint of claim 19, wherein the annular member is sidewalls integrally formed with the cap portion.

21. The combination end seal and cotyledon restraint of claim 19, wherein the annular member is sized and configured for sealing engagement with an outside perimeter of a seed coat.

22. The combination end seal and cotyledon restraint of claim 19, wherein the annular member is sized and configured for sealing engagement with an interior perimeter of a seed coat.

23. The combination end seal and cotyledon restraint of claim 20, wherein the sidewalls form a cylindrical housing having an interior sized and configured to shelter a nutritive media.

24. The combination end seal and cotyledon restraint of claim 23, wherein the interior of the housing is contoured.

25. The combination end seal and cotyledon restraint of claim 20, wherein the sidewalls are tapered.

26. A combination end seal and cotyledon restraint for an artificial seed, the combination end seal and cotyledon restraint comprising:
(a) means for substantially sealing an end of an artificial seed; and
(b) a cotyledon restraint integrally formed with the means for sealing an end of an artificial seed.

* * * * *